United States Patent
Otsuka

(10) Patent No.: US 10,835,188 B2
(45) Date of Patent: Nov. 17, 2020

(54) ROBOT PROVIDING HEALTH SUPPORT WITH COMMUNICATION, ROBOT CONTROL METHOD, AND NON-TRANSITORY RECORDING MEDIUM

(71) Applicant: CASIO COMPUTER CO., LTD., Tokyo (JP)

(72) Inventor: Toshihiko Otsuka, Tokyo (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 568 days.

(21) Appl. No.: 15/667,328

(22) Filed: Aug. 2, 2017

(65) Prior Publication Data
US 2018/0085071 A1   Mar. 29, 2018

(30) Foreign Application Priority Data

Sep. 23, 2016  (JP) ................................. 2016-186083

(51) Int. Cl.
*A61B 5/00*     (2006.01)
*A61B 5/0205*   (2006.01)
(Continued)

(52) U.S. Cl.
CPC ........ *A61B 5/7475* (2013.01); *A61B 5/02055* (2013.01); *A61B 5/02444* (2013.01);
(Continued)

(58) Field of Classification Search
CPC combination set(s) only.
See application file for complete search history.

(56) References Cited

U.S. PATENT DOCUMENTS 9,126,122 B2 *   9/2015   Boeckle ................... A63H 3/28
2002/0183598 A1 *  12/2002  Teraura ................ A61B 5/6896
                                                           600/300
(Continued)

FOREIGN PATENT DOCUMENTS

CN    204797811 U     11/2015
JP    2003-135410 A    5/2003
(Continued)

OTHER PUBLICATIONS

JPO; Application No. 2016-186083; Notification of Reasons for Refusal dated Aug. 28, 2018.
(Continued)

*Primary Examiner* — Michael W Kahelin
*Assistant Examiner* — Shirley X Jian
(74) *Attorney, Agent, or Firm* — Fitch, Even, Tabin & Flannery LLP

(57) ABSTRACT

Provided are a robot, a robot control method, and a non-transitory recording medium capable of causing a predetermined object to continuously have a health support without having a consciousness of a diagnosis. The robot includes an obtainer (a sensor set) obtaining biometric information of a predetermined object in accordance with a touch by the predetermined object to the robot without requesting the predetermined object to touch the robot, the biometric information being obtained by the touch of the predetermined object, a determiner determining the biometric information obtained by the obtainer, and a controller controlling the robot based on a determined result by the determiner.

14 Claims, 9 Drawing Sheets

(51) Int. Cl.
  *G16H 40/63* (2018.01)
  *A61B 5/024* (2006.01)
  *A61B 5/01* (2006.01)
  *A61B 5/021* (2006.01)
  *G06F 19/00* (2018.01)
  *G06Q 50/24* (2012.01)

(52) U.S. Cl.
  CPC .......... *A61B 5/6886* (2013.01); *A61B 5/6896* (2013.01); *A61B 5/744* (2013.01); *G16H 40/63* (2018.01); *A61B 5/0002* (2013.01); *A61B 5/01* (2013.01); *A61B 5/021* (2013.01); *A61B 5/024* (2013.01); *A61B 5/6898* (2013.01); *A61B 5/7455* (2013.01); *G06F 19/3418* (2013.01); *G06Q 50/24* (2013.01)

(56) References Cited

U.S. PATENT DOCUMENTS

2010/0121162 A1* 5/2010 Klinke .............. A61B 5/14532
                                                    600/309
2012/0295510 A1* 11/2012 Boeckle .............. A61B 5/6896
                                                    446/72
2013/0095721 A1* 4/2013 Poon ...................... A63H 3/02
                                                    446/72
2016/0029962 A1* 2/2016 Hyde .................... A61B 5/117
                                                    600/301
2016/0029963 A1* 2/2016 Hyde ................... A61B 5/7475
                                                    600/301

FOREIGN PATENT DOCUMENTS

| | | |
|---|---|---|
| JP | 2003-284695 A | 10/2003 |
| JP | 2004-357915 A | 12/2004 |
| JP | 2006-92356 A | 4/2006 |
| JP | 2016-165415 A | 9/2016 |

OTHER PUBLICATIONS

CNIPA; Application No. 201710699362.8; Office Action dated Oct. 30, 2019.

* cited by examiner

FIG.1A
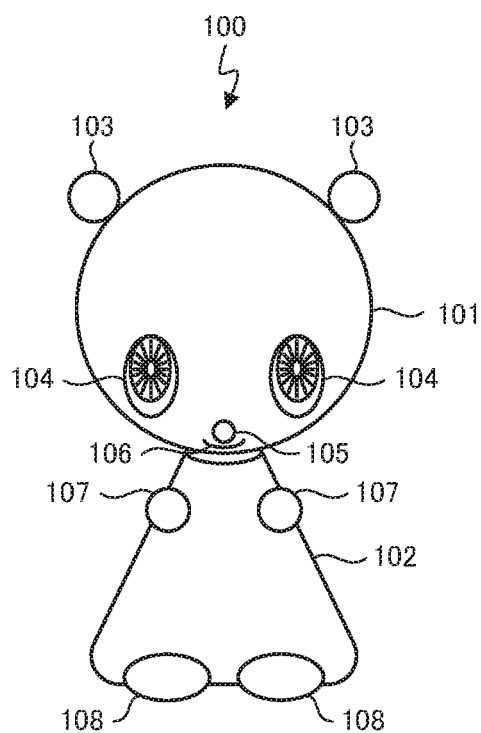
FIG.1B
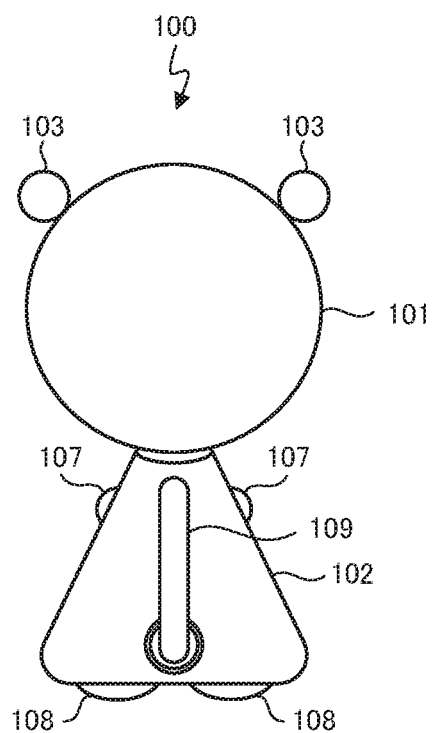
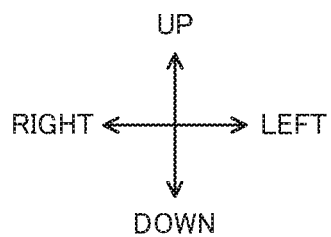
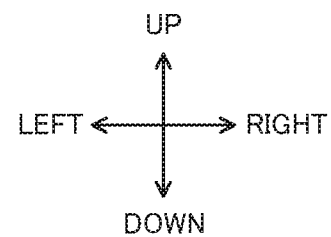

FIG.3

DETERMINING CRITERION TABLE

| VITAL SIGN | AVERAGE VALUE | UPPER LIMIT THRESHOLD | LOWER LIMIT THRESHOLD | |
|---|---|---|---|---|
| BODY TEMPERATURE [°C] | 36.6 | 37.3 | 35.8 | |
| PULSE [bpm] | 71 | 89 | 53 | |
| BLOOD PRESSURE [mmHg] | 115/83 | 138/100 | 92/66 | ↓ UPDATE |
| BODY TEMPERATURE [°C] | 36.6 | 37.3 | 35.8 | |
| PULSE [bpm] | 71 | 89 | 53 | |
| BLOOD PRESSURE [mmHg] | 115/83 | 138/100 | 92/66 | ↓ UPDATE |
| ⋮ | ⋮ | ⋮ | ⋮ | |

FIG.4

CORRESPONDING ACTION DETERMINING TABLE

| VITAL SIGN | DETERMINED RESULT | CORRESPONDING ACTION | |
|---|---|---|---|
| BODY TEMPERATURE | WITHIN NORMAL RANGE | SHAKE TAIL GREATLY | MR111 |
| | | NOD | MR112 |
| | | ⋮ | ⋮ |
| | EXCEEDING UPPER LIMIT THRESHOLD | REPORT THAT BODY TEMPERATURE IS HIGH | MR121 |
| | | DECREASE BODY TEMPERATURE | MR122 |
| | | ⋮ | ⋮ |
| | BELOWING LOWER LIMIT THRESHOLD | REPORT THAT BODY TEMPERATURE IS LOW | MR131 |
| | | INCREASE BODY TEMPERATURE | MR132 |
| | | ⋮ | ⋮ |
| PULSE | WITHIN NORMAL RANGE | OPEN MOUSE | MR211 |
| | | NOD | MR212 |
| | | ⋮ | ⋮ |
| | EXCEEDING UPPER LIMIT THRESHOLD | VIBRATE SLOWLY | MR221 |
| | | CLOSE EYELID | MR222 |
| | | ⋮ | ⋮ |
| | BELOWING LOWER LIMIT THRESHOLD | VIBRATE QUICKLY | MR231 |
| | | BLINK | MR232 |
| | | ⋮ | ⋮ |
| BLOOD PRESSURE | WITHIN NORMAL RANGE | SPREAD HANDS | MR311 |
| | | NOD | MR312 |
| | | ⋮ | ⋮ |
| | EXCEEDING UPPER LIMIT THRESHOLD | REPORT THAT BLOOD PRESSURE IS HIGH | MR321 |
| | | CLOSE EYELID | MR322 |
| | | ⋮ | ⋮ |
| | BELOWING LOWER LIMIT THRESHOLD | REPORT THAT BLOOD PRESSURE IS LOW | MR331 |
| | | WAVE HANDS HORIZONTALLY | MR332 |
| | | ⋮ | ⋮ |

FIG.5

MEASUREMENT RECORD TABLE

| No. | TOUCH DATE AND TIME | TOUCH PART | ACTION MODE | BODY TEMPERATURE [°C] | PULSE [bpm] | BLOOD PRESSURE (MAX/MIN) [mmHg] | DETERMINED RESULT | VARIOUS ACTIONS (FIRST TOUCH MAINTAINING ACTION/ SECOND TOUCH MAINTAINING ACTION/ CORRESPONDING ACTION) |
|---|---|---|---|---|---|---|---|---|
| 1 | 2016.01.12 10:03 | HEAD | NORMAL | 36.4 | 66 | 118/82 | WITHIN NORMAL RANGE | -/-/MR111 |
| 2 | 2016.01.13 10:12 | HEAD | NORMAL | 36.3 | 71 | 120/90 | WITHIN NORMAL RANGE | -/-/MR212 |
| 3 | 2016.01.15 15:20 | HAND | MAINTAIN | 35.9 | 100 | 140/91 | PULSE: EXCEEDING UPPER LIMIT THRESHOLD | MC121/-/MR221 |
| 4 | 2016.01.20 20:05 | BODY | NORMAL | 36.0 | 70 | 135/88 | BLOOD PRESSURE (UPPER): EXCEEDING UPPER LIMIT THRESHOLD | -/-/MR321 |
| 5 | 2016.01.21 10:23 | HAND | MAINTAIN | 36.2 | 65 | 136/86 | WITHIN NORMAL RANGE | MC131/MC232/MR212 |
| 6 | 2016.01.23 09:31 | HEAD | NORMAL | 37.5 | 60 | 121/80 | BODY TEMPERATURE: EXCEEDING UPPER LIMIT THRESHOLD | -/-/MR121 |
| 7 | 2016.01.26 10:03 | BODY | MAINTAIN | 36.5 | 62 | 120/79 | WITHIN NORMAL RANGE | MC122/MC221/MR311 |
| 8 | 2016.01.26 12:56 | BODY | NORMAL | 36.0 | 102 | 120/82 | PULSE: EXCEEDING UPPER LIMIT THRESHOLD | -/-/MR222 |
| 9 | 2016.01.29 10:13 | HEAD | MAINTAIN | 36.5 | 62 | 145/91 | BLOOD PRESSURE (UPPER); BELOWING LOWER LIMIT THRESHOLD | MC113/-/MR331 |
| 10 | 2016.01.31 11:38 | HAND | NORMAL | 37.0 | 61 | 125/79 | WITHIN NORMAL RANGE | -/-/MR111 |
| ... | ... | ... | ... | ... | ... | ... | ... | ... |

FIG. 6

TOUCH MAINTAINING ACTION DETERMINING TABLE

| TOUCH PART | FIRST TOUCH MAINTAINING ACTION | | SECOND TOUCH MAINTAINING ACTION | |
|---|---|---|---|---|
| HEAD | SLOWLY STOP MOTIONS OF HEAD AND HAND | MC111 | MOVE SO AS TO COME CLOSE TO PREDETERMINED OBJECT | MC211 |
| | GRADUALLY CHANGE TO JOYFUL EXPRESSION | MC112 | GRANTED EXPRESSION | MC212 |
| | SING | MC113 | OUTPUT SOUND PROMPTING PREDETERMINED OBJECT TO MAINTAIN TOUCH | MC213 |
| | ... | ... | ... | ... |
| BODY | SLOWLY STOP MOTION OF TAIL | MC121 | MOTION LIKE RUNNING WILD | MC221 |
| | GRADUALLY CHANGE TO PEACEFUL EXPRESSION | MC122 | MOTION LIKE SHAKING | MC222 |
| | SLOWLY CLOSE EYELID | MC123 | OUTPUT SOUND PROMPTING PREDETERMINED OBJECT TO MAINTAIN TOUCH | MC223 |
| | ... | ... | ... | ... |
| HAND | SLOWLY STOP MOTION OF TAIL | MC131 | SHAKE HEAD HORIZONTALLY | MC231 |
| | GRADUALLY CHANGE TO PLEASANT EXPRESSION | MC132 | DISAPPOINTED EXPRESSION | MC232 |
| | SLOWLY AND LARGELY NOD | MC133 | OUTPUT SOUND PROMPTING PREDETERMINED OBJECT TO MAINTAIN TOUCH | MC233 |
| | ... | ... | ... | ... |

ROBOT PROVIDING HEALTH SUPPORT WITH COMMUNICATION, ROBOT CONTROL METHOD, AND NON-TRANSITORY RECORDING MEDIUM

CROSS-REFERENCE TO RELATED APPLICATION

This application claims the benefit of Japanese Patent Application No. 2016-186083, filed on Sep. 23, 2016, the entire disclosure of which is incorporated by reference herein.

FIELD

This application relates generally to a robot providing health support with communication, a robot control method, and a non-transitory recording medium.

BACKGROUND

Technologies relating to robots that provide health support while communicating with a predetermined object like a user are widely known. For example, Unexamined Japanese Patent Application Kokai Publication No. 2003-284695 discloses a pet robot that collects biometric information from the predetermined object by periodically performing an action of intentionally prompting the predetermined object to touch a touch surface in which a biometric measurement device is built, and reporting the predetermined object of a diagnostic result based on the collected biometric information by voice.

SUMMARY

A robot according to an aspect of a present invention includes a processor and body parts with the processor configured to: obtain biometric information of an object from a touch part of the body parts of the robot touched by the object without requesting the object to touch the robot, wherein the biometric information is obtained by the touch of the object; determine the biometric information obtained; control the robot based on a determined result; control, in a case that the biometric information is not obtained due to an insufficient touch time by the object, at least one of the body parts of the robot to perform an action to welcome the touch by the object as a first maintaining action for maintaining the object to touch in such a way that the touch time by the object becomes equal to or longer than a time period necessary to obtain the biometric information; determine that the touch by the object is likely to be released; and control, in a case that the first maintaining action has been performed and the processor determines that the touch by the object is likely to be released, the at least one of the body parts, at least another one of the body parts, or both, of the robot to perform a second maintaining action that is different from the first maintaining action and requests the object to touch the robot.

A robot control method according to another aspect of the present invention includes: obtaining biometric information of an object in accordance with a touch by the object to the robot without requesting the object to touch the robot, the biometric information being obtained by the touch of the object; determining the obtained biometric information; and controlling the robot based on a determined result by the determination on the biometric information; controlling, in a case that the biometric information is not obtained due to an insufficient touch time by the object, the robot to perform an action to welcome the touch by the object as a first maintaining action for maintaining the object to touch in such a way that the touch time by the object becomes equal to or longer than a time period necessary to obtain the biometric information; determining that the touch by the object is likely to be released; and controlling, in a case that the first maintaining action has been performed and the processor determines that the touch by the object is likely to be released, the robot to perform a second maintaining action that is different from the first maintaining action and requests the object to touch the robot.

A non-transitory computer readable recording medium according to the other aspect of the present invention has stored therein a program that causes a computer to accomplish a robot control function, the program causing the computer of the robot to: obtain biometric information of an object in accordance with a touch by the object to the robot without requesting the object to touch the robot, the biometric information being obtained by the touch of the object; determine the obtained biometric information; control the robot based on a determined result by the determination on the biometric information; control, in a case that the biometric information is not obtained due to an insufficient touch time by the object, the robot to perform an action to welcome the touch by the object as a first maintaining action for maintaining the object to touch in such a way that the touch time by the object becomes equal to or longer than a time period necessary to obtain the biometric information; determines that the touch by the object is likely to be released; and control, in a case that the first maintaining action has been performed and the processor determines that the touch by the object is likely to be released, the robot to perform a second maintaining action that is different from the first maintaining action and requests the object to touch the robot.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1A is a front external view of a robot according to an embodiment of the present disclosure;

FIG. 1B is a rear external view of the robot according to the embodiment of the present disclosure;

FIG. 3 is a diagram illustrating an example of a determining criterion table;

FIG. 4 is a diagram illustrating an example of a corresponding action determining table;

FIG. 5 is a diagram illustrating an example of a measurement record table;

FIG. 6 is a diagram illustrating an example of a touch maintaining action determining table;

DETAILED DESCRIPTION

Figure 2:
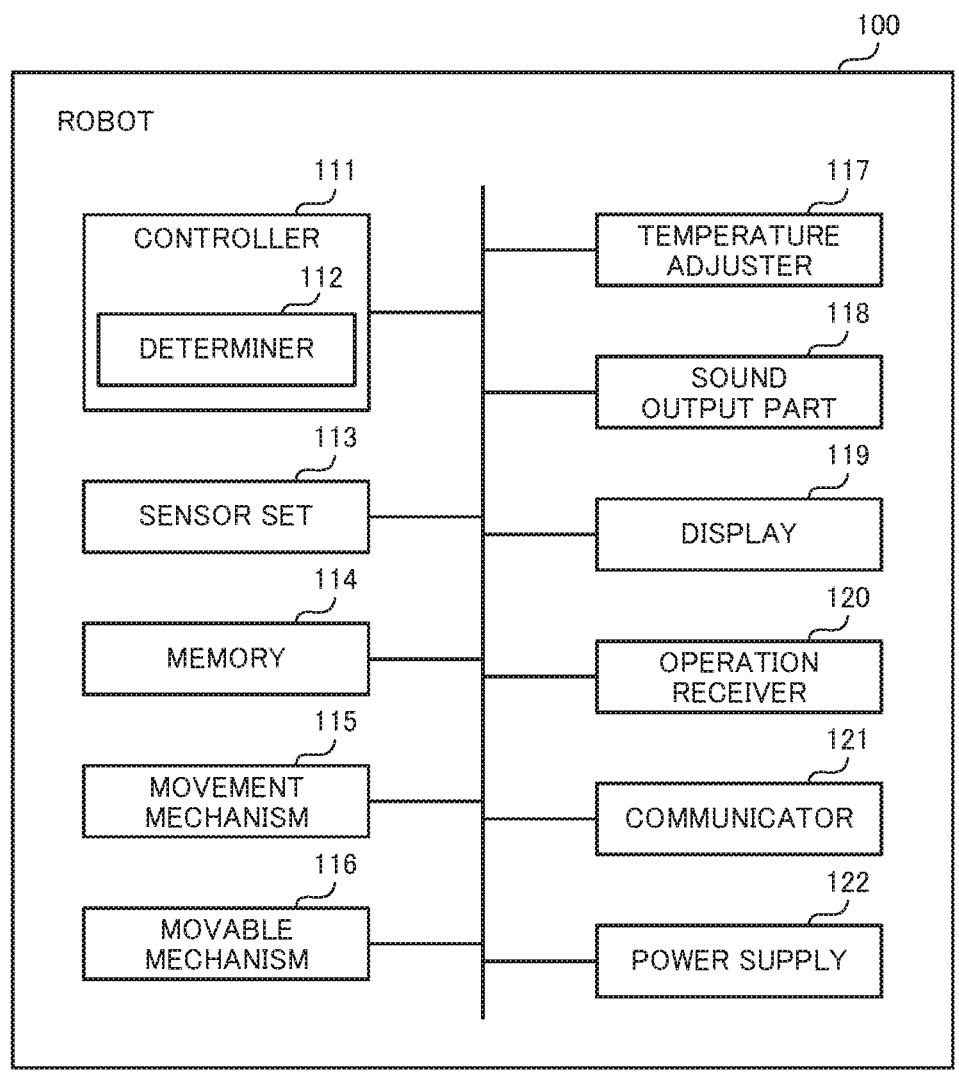
FIG. 2 is a block diagram illustrating a functional structure of the robot.

A robot according to an embodiment of the present disclosure will be described below with reference to the figures.

A robot 100 according to the embodiment of the present disclosure obtains a measured value of a vital sign as biometric information from a predetermined object in response to a touch by the predetermined object, and assists the predetermined object so as to maintain and improve a health state thereof to a normal condition. In this case, a typical predetermined object is a human, but may be various animals to be kept as pets. In addition, the health state is generally a physical state and a psychological state that can be determined or estimated based on the measured values of vital signs.

As illustrated in FIGS. 1A and 1B, the robot 100 has a three-dimensional shape imitating a small dog in appearance. In addition, the exterior components of the robot 100 are mainly formed of a metallic material, and a resin material having thermal conductivity. The robot 100 includes a head 101, a body 102, a pair of right and left hands 107, a pair of right and left legs 108, and a tail 109. In addition, the head 101 has a pair of right and left ears 103, a pair of right and left eyes 104, a nose 105, and a mouth 106. The mouth 106 employs a general mechanism that changes the shape of an opening provided in the lower portion of the head 101, and shows various expressions by changing the shape of the opening.

As illustrated in FIG. 2, the robot 100 functionally includes a controller 111, a determiner 112, a sensor set 113, a memory 114, a movement mechanism 115, a movable mechanism 116, a temperature adjuster 117, a sound output part 118, a display 119, an operation receiver 120, a communicator 121, and a power supply 122. These components are electrically connected to each other via a bus line or the like.

The controller 111 controls the whole operation of the robot 100. The controller 111 is accomplished by a microcomputer that includes a central processing unit (CPU), a read only memory (ROM), and a random access memory (RAM). The controller 111 controls the action of each component of the robot 100 by causing the CPU to read action programs stored in the ROM and to execute the programs on the RAM.

By executing the action programs, the controller 111 generates a control signal for moving the robot 100 based on, for example, various data obtained from the sensor set 113, and transmits the control signal to the movement mechanism 115, thereby controlling the movement action of the robot 100.

In addition, by executing the action programs, the controller 111 determines whether or not the measured value of vital signs as the biometric information of the predetermined object can be obtained via the sensor set 113 in response to, for example, the touch by the predetermined object (determination on obtainment of the biometric information). Hence, the controller 111 functions as a judgement part.

Still further, the controller 111 accomplishes the function corresponding to the determiner 112 by executing the action programs.

The determiner 112 determines various states, such as physical and mental condition of the predetermined object and status of the robot 100, based on the various data obtained from the sensor set 113. For example, the determiner 112 sets a determining criterion based on the measured value of the vital sign obtained as the biometric information of the predetermined object from the sensor set 113, and determines a compared result between this determining criterion and the measured value of the vital sign obtained at the present time. In addition, the determiner 112 detects a change in the motion of the robot 100 and the direction thereof based on, for example, detection data by an acceleration sensor and an angular velocity sensor in the sensor set 113, and determines the status of the robot 100.

Note that the controller 111 and the determiner 112 may be accomplished by a single microcomputer or may be individually accomplished by individual microcomputers.

The sensor set 113 obtains various kinds of information (physical quantity) indicating the internal status and external status of the robot 100, converts such information into a predetermined signal as appropriate, and supplies the to the controller 111. The sensor set 113 includes various sensors, such as a vital sensor that measures the vital sign which is a sign indicating the life sustainment, the acceleration sensor and the angular velocity sensor that measure motion and direction of the robot 100, a distance sensor that measures the distance between the robot 100 and the predetermined object, a temperature sensor that measures the surface temperature of the exterior component of the robot 100, and an image sensor to grasp the external situation of the robot 100, and a microphone that collects sounds. In this embodiment, the vital sensor measures a body temperature, a pulse, and a blood pressure in accordance with the touch by the predetermined object, and outputs these measured values to the controller 111 as the biometric information of the predetermined object. The vital sensor and the temperature sensor are disposed in the head 101, the body 102, and the hand 107. In addition, the acceleration sensor and the angular velocity sensor are disposed on the body 102, the distance sensor and the image sensor are disposed on the head 101 near the eye 104, and the microphone is disposed in the ear 103, as appropriate. Hence, the sensor set 113 functions as an obtainer that obtains the biometric information, and the like, of the predetermined object.

The memory 114 stores various data necessary for the controller 111 to control each component of the robot 100. The memory 114 includes, for example, a non-volatile memory device, such as a flash memory or a hard disk drive (HDD). The memory 114 stores, for example, a determining criterion table, a corresponding action determining table, a measurement record table, and a touch maintaining action determining table in respective predetermined memory areas.

The determining criterion table illustrated in FIG. 3 is a table that sets a criterion for determining the measured value of the vital sign. The controller 111 (determiner 112) sets each numerical value in the determining criterion table based on the measured value of the vital sign obtained from the vital sensor of the sensor set 113. The determining criterion table is constructed so as to associate numerical data that is "average value", "upper limit threshold", "lower limit threshold" with each item of "vital sign" (the body temperature, the pulse, and the blood pressure). The numerical value of the blood pressure indicates each numerical value of maximum blood pressure (systolic blood pressure) indicated when the heart contracts, and minimum blood pressure (diastolic blood pressure) indicated when the heart expands.

The "average value" is an average value of multiple measured values for each item of the vital signs. The "upper limit threshold" and "lower limit threshold" are limit values for the allowable range as the measured values of the vital signs. The "upper limit threshold" and the "lower limit threshold" are set based on the average value, and are automatically calculated by, for example, multiplying the average value by a predetermined ratio (for example, 1.05 in the case of the upper limit threshold, and 0.95 in the case of the lower limit threshold). These determining criteria are calculated and updated every time the measured value of vital signs is obtained by a predetermined number of times. Note that these determining criteria may be calculated and updated every time a predetermined time has elapsed regardless of the number of obtainments of the measured values.

The corresponding action determining table illustrated in FIG. 4 is a table that sets a corresponding action to be executed by the robot 100 in accordance with the touch by the predetermined object. The corresponding action determining table associates pieces of data with each other which are "determined result" and "corresponding action" for each item of the vital sign.

The "determined result" is a compared result between the measured value of the vital sign obtained at the present time with each numerical value of the "upper limit threshold" and the "lower limit threshold" in the determining criterion table illustrated in FIG. 3, and is classified into "within normal range", "exceeding upper limit threshold", and "exceeding lower limit threshold". "within normal range" indicates that the measured value of the vital sign obtained at the present time falls into the range (normal range) between the upper limit threshold and the lower limit threshold, and indicates the normal condition. "Exceeding upper limit threshold" indicates that the measured value of the vital sign obtained at the present time exceeds the upper limit threshold. "Exceeding lower limit threshold" indicates that the measured value of the vital sign obtained at the present time exceeds the lower limit threshold.

The "corresponding action" is the details of an action to be executed in accordance with the touch by the predetermined object. Multiple actions are prepared for each determination result in the "corresponding action". For example, as illustrated in FIG. 3, as for the determined result "within normal range" regarding the item "body temperature" of the "vital sign", the "corresponding actions" that are "shaking the tail more" and "nodding" are set. In addition, an identification code ("MR 111" or the like) for identifying such the action is assigned to each corresponding action.

For example, when the determination result for the item "body temperature" is "exceeding upper limit threshold" and the selected corresponding action is "decreasing temperature", the controller 111 refers to the temperature data of the temperature sensor in the sensor set 113, and transmits a control signal to the temperature adjuster 117 so as to cool down the exterior component of the robot 100 by a Peltier element. Moreover, when, for example, the determination result for the item "body temperature" is "exceeding lower limit threshold", and the selected corresponding action is "increasing temperature", the controller 111 refers to the temperature data of the temperature sensor in the sensor set 113, and transmits a control signal to the temperature adjuster 117 so as to warm up the exterior component of the robot 100 by a heater.

When the determined result is "exceeding upper limit threshold" or "exceeding lower limit threshold", an action of reporting the predetermined object of the determination result (for example, "reporting that the blood pressure is high") is set as the "corresponding action", but this reporting action may be set so as to also present any improved behavior (for example, prompting a deep breath). In addition, weighting may be assigned to each action by, for example, assigning a different determining ratio to each corresponding action.

When, for example, the determination result for the item "blood pressure" is "exceeding upper limit threshold", and the corresponding action is "reporting that the blood pressure is high", the controller 111 controls the sound output part 118 and the display 119 so as to report the measured value of the blood pressure and the improved behavior by sound and text. In this manner, the controller 111, the sound output part 118, and the display 119 function as a reporter.

The measurement record table illustrated in FIG. 5 is a table that summarizes a touch date and time by the predetermined object, the measurement of the vital sign of the predetermined object, the corresponding action executed by the robot 100, and the like in time series. As illustrated in FIG. 5, the contact history table stores respective pieces of data in association with each other which are "touch date and time", "touch part", "action mode", the "body temperature", "pulse", "blood pressure", "determined result", and "various actions".

The "touch date and time" indicates the date and the time at which the touch by the predetermined object was detected. The "touch part" is a part of the robot 100 capable of detecting the touch by the predetermined object, and is classified into three parts that are "head", "body", and "hand". Expected ways of the touch by the predetermined object are, for example, a hand of the predetermined object is placed on the upper surface of the head 101, the lower portion of the head 101 (near the lower part of a jaw) is rubbed, the body 102 is held and lifted, the body 102 is folded, and the hand 107 is held.

The "action mode" indicates a type of the action mode when the action relative to the touch by the predetermined object is executed. The robot 100 executes the action relative to the touch by the predetermined object in a different action mode in accordance with the obtainment situation of the vital sign. As for this action mode, for example, a normal action mode and a touch maintaining action mode are prepared. Normally, the action mode is set to be the normal action mode. At this time, for example, the robot 100 stops the motion of the touch part as the action relative to the touch by the predetermined object. Conversely, when a phenomenon such that the vital sign cannot be obtained due to the insufficient time of the touch by the predetermined object occurs, the action mode is set and changed from the normal action mode to the touch maintaining action mode. At this time, the robot 100 performs a touch maintaining action to be described later. In the measurement record table illustrated in FIG. 5, "normal" indicates the normal action mode, and "maintain" indicates the touch maintaining action mode.

The "body temperature", the "pulse", and the "blood pressure" indicate the measured values of the respective items of the vital sign obtained in accordance with the touch by the predetermined object. The "various actions" indicate various actions performed by the robot 100, and the respective identification codes are stored in the order of a first touch maintaining action, a second touch maintaining action, and the corresponding action to be described later.

The measurement record table is updated every time the measured value of the vital sign is obtained in accordance with the touch by the predetermined object.

The touch maintaining action determining table illustrated in FIG. 6 is a table that sets the touch maintaining action to be executed when the action mode relative to the touch by the predetermined object is the touch maintaining action mode. In this case, in order to obtain an effective measured value from the vital sensor, a touch time (time from the start of touch to the end thereof) that is longer than the time (necessary measurement time) necessary for the measurement by the vital sensor should be ensured. Hence, the robot 100 executes the touch maintaining action as an action for maintaining the predetermined object to touch the robot 100 as long as possible. The touch maintaining action determining table associates respective pieces of data with each other which are "first touch maintaining action" and "second touch maintaining action" for each "touch part".

The "touch part" is consistent with the "touch part" in the corresponding action table described above. The "first touch maintaining action" indicates an action to be executed to maintain the predetermined object to touch when the action mode relative to the touch by the predetermined object is the touch maintaining action mode. The "second touch maintaining action" indicates an action to be executed instead of the first touch maintaining action when the touch by the predetermined object is expected and is likely to be released during the execution of the first touch maintaining action. In addition, each corresponding action is assigned with an identification code (for example, "MC111") to identify the action.

As illustrated in FIG. 6, as for the "first touch maintaining action", actions to welcome the touch by the predetermined object, such as "slowly stopping the motion of the head or the hand" or "gradually changing to a pleasing expression", are set. In addition, as for the "second touch maintaining action", an action for requesting the predetermined object to maintain the touch, such as "moving so as to approach the predetermined object" or "outputting a sound to prompt the predetermined object to maintain the touch (for example, outputting a voice like "keep holding"), is set. In addition, in the case in which "outputting sound to prompt the predetermined object to maintain the touch" is selected as the second touch maintaining action, in addition to the sound output, the controller 111 may control the display 119 to display a message (text) prompting the predetermined object to maintain the touch.

The movement mechanism 115 is a part to move the robot 100. The movement mechanism 115 includes a pair of right and left wheels provided at the respective bottoms of the pair of right and left legs 108 of the robot 100, a motor that rotates and drives the pair of right and left wheels, and a drive circuit that drives and controls the motor. In accordance with the control signal received from the controller 111, the drive circuit supplies drive pulse signals to the motor. The motor rotates and drives the pair of right and left wheels to move the robot 100 in accordance with the drive pulse signals. Thus, the movement mechanism 115 functions as an action part that moves the robot 100. Note that the number of motors is optional as long as the pair of left and right wheels is configured to be independently rotated and driven and the robot 100 can move forward, backward, turn, accelerate and decelerate. For example, the pair of right and left wheels may be driven by a single motor and by providing a linkage mechanism and a steering mechanism. In addition, the number of drive circuits can be changed as appropriate in accordance with the number of motors.

The movable mechanism 116 is a part that performs a predetermined motion under the control by the controller 111. The movable mechanism 116 includes driven members such as the head 101, the hands 107, the legs 108, and the tail portion 109, driving members, such actuators to drive the driven members, and a drive circuit that drives and controls the driving members. Under the control by the controller 111, the movable mechanism 116 causes the drive member to drive the driven member in accordance with the drive signal supplied from the drive circuit, thereby performing actions, such as moving the hands and legs, and swinging the head up and down, and right and left. Hence, the movable mechanism 116 functions as an action part to cause the robot 100 to perform an action. In addition to the movement mechanism 115 and the movable mechanism 116, the sound output part 118 and the display 119 also function as the action part.

The temperature adjuster 117 is a part to change the temperature of the exterior component of the robot 100. The temperature adjuster 117 includes, for example, the heater that heats the exterior component of the robot 100, and the Peltier element that cools down the exterior component of the robot 100. The Peltier element may be used as a member that heats the exterior of the robot 100. Hence, the temperature adjuster 117 functions as a temperature changer that changes the temperature of the robot 100.

The sound output part 118 includes a speaker and a sound output interface, converts sound data generated by the controller 111 into sound, and outputs the sound to the exterior. The speaker is installed in a condition of, for example, being fitted in the mouth 106. The robot 100 collects sounds of the predetermined object by the microphone in the sensor set 113, and outputs sounds corresponding to the uttered details by the predetermined object from the sound output part 118 under the control by the controller 111, thus capable of having a simple conversation with the predetermined object.

The display 119 includes, a display screen interface like a liquid crystal display (LCD) or an organic EL (Electro-Luminescent) display, and a display driver, digitally displays data or the like relating to the various functions. The display driver outputs a drive signal corresponding to the type of the display screen to the display screen interface based on the control signal from the controller 111, and displays information of the display screen.

The operation receiver 120 receives an input operation from the predetermined object, and outputs electric signals corresponding to the input operation to the controller 111 as input signals. Note that the operation receiver 120 may be a touch panel including a display screen of the display 119, and a touch sensor laid over on the display screen. In this case, the operation receiver 120 outputs, to the controller 111, an operation signal in accordance with a detected result by the touch sensor, such as a touch position and a touch way relating to the touch action by the user on the touch panel.

The communicator 121 includes a wireless communication module, and an antenna, and performs data communication with an external device.

The power supply 122 includes a power supply circuit, a battery, and the like, and supplies power to each component of the robot 100 in accordance with an instruction from the controller 111.

Next, with reference to a flowchart that is FIG. 7, a touch corresponding action process to be executed by the robot 100 will be described. The touch corresponding action process is a process of determining and executing the action of the robot 100 relative to the touch by the predetermined object. In response to power loading of the robot 100 by the operation by the predetermined object, the controller 111 starts the touch corresponding action process.

When starting the touch corresponding action process, first, the controller 111 reads initial data stored in a predetermined memory area of the memory 114, and sets each component of the robot 100 to be an initial state (step S101). Next, the controller 111 controls the movement mechanism 115 and the movable mechanism 116 to cause the robot 100 to run at random in the space where the robot 100 is utilized, or to slightly wobble or swing the head 101, the hands 107, the legs 108, the tail 109 so as to perform a predetermined action similar to the action by an actual pet.

Next, the controller 111 reads the measurement record table stored in the memory 114, and obtains record information of the vital signs (step S102).

Subsequently, the controller 111 determines whether or not the measured value data of the vital signs has insufficiency (step S103). When, for example, there is no obtained record of the measured value data of the vital sign for a predetermined past time (for example, several hours to several days) in the obtained record information, the controller 111 determines that the measured value data of the vital sign has insufficiency.

Figure 8:
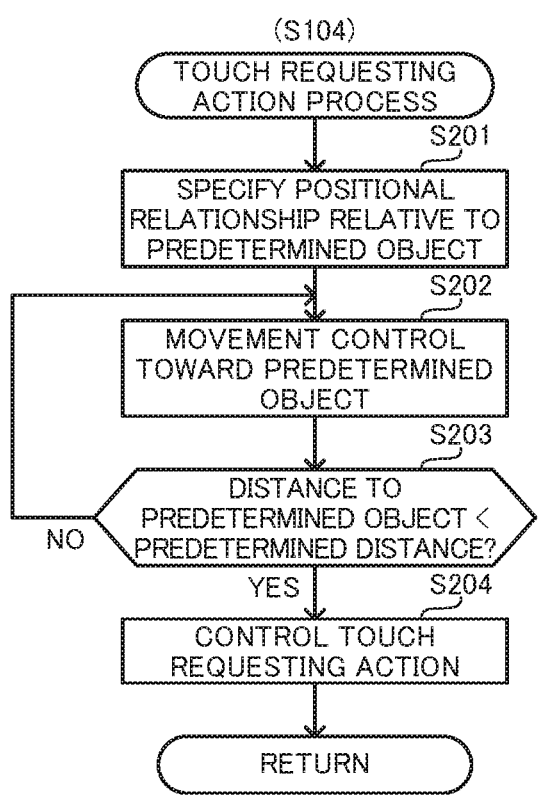
FIG. 8 is a flowchart illustrating a flow of a touch requesting action process.

When determining that the measured value data of the vital signs has insufficiency (step S103: YES), the controller 111 executes a touch requesting action process (step S104). In this case, with reference to a flowchart that is FIG. 8, the touch requesting action process will be described. The touch requesting action process is a process of executing an action of requesting the predetermined object to touch in order to collect the measured data of the vital signs.

When starting the touch requesting action process, first, the controller 111 specifies a relative positional relationship between the robot 100 and the predetermined object (step S201). The controller 111 specifies the relative positional relationship between the robot 100 and the predetermined object based on various pieces of data (for example, distance data of the distance sensor) obtained from the sensor set 113. Next, the controller 111 transmits the control signal for moving the robot 100 to the movement mechanism 115, and moves the robot 100 toward the predetermined object while controlling the movement action by the movement mechanism 115 (step S202).

The controller 111 determines whether or not the distance between the robot 100 and the predetermined object is shorter than a predetermined distance (for example, 30 cm) (step S203), and when the distance between the robot 100 and the predetermined object is greater than the predetermined distance or when the distance is equal to the predetermined distance (step S203: NO), the controller 111 keeps controlling the movement mechanism 115 until the distance between the robot 100 and the predetermined object becomes smaller than the predetermined distance. When determining that the robot 100 has approached so that the distance between the robot 100 is smaller than the predetermined distance (step S203: YES), the controller 111 controls the movable mechanism 116 to perform the action for requesting the predetermined object of the touch (step S204). The action for requesting the predetermined object of the touch involves various actions, such as an action to stretch forth the hand 107 to get hand shaking, and to move down the head 101 so as to be rubbed. After executing the process in the step S204, the controller 111 terminates the touch requesting action process.

Figure 7:
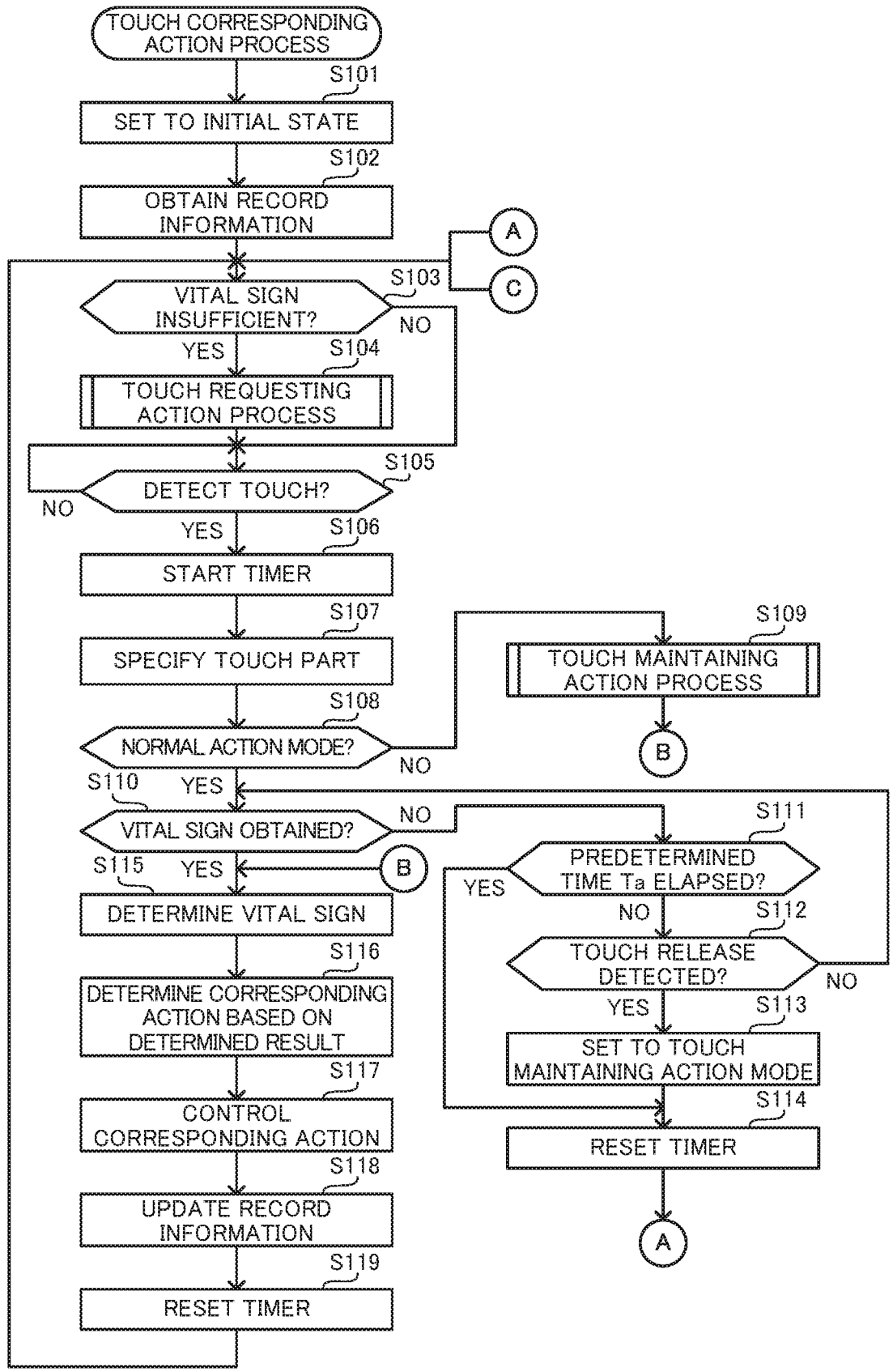
FIG. 7 is a flowchart illustrating a flow of a touch corresponding action process.

Returning to the flowchart for the touch corresponding action process illustrated in FIG. 7, after performing the touch requesting action process, or, when determining as NO in the step S103, the controller 111 determines whether or not the touch by the predetermined object is detected (step S105). The controller 111 detects, for example, presence or absence of the touch by the predetermined object in accordance with a change in the measured value of the vital sensor in the sensor set 113. When detecting no touch by the predetermined object (step S105: NO), the controller 111 stands by until detecting the touch by the predetermined object. When detecting no touch by the predetermined object even after a predetermined time has elapsed, the controller 111 may execute the above touch requesting process as appropriate.

When determining that the touch by the predetermined object is detected (step S105: YES), the controller 111 starts a timer count to measure the touch time by the predetermined object (step S106).

The controller 111 specifies the touch part that is touched by the predetermined object (step S107). The controller 111 specifies the touch part in according with from which vital sensor the measured value indicating the detection of the touch is obtained and on which part such a sensor is disposed. The controller 111 may consider, when specifying the touch part, a change in the acceleration data in three axial directions (X-axis direction, Y-axis direction and Z-axis direction) obtained from the acceleration sensor. The controller 111 specifies any of the head 101, the body 102, the hand 107 where the vital sensor is disposed as the touch part by the predetermined object.

Subsequently, the controller 111 determines, whether or not the action mode after the touch by the predetermined object is detected and until the measured values of vital signs is the normal action mode (step S108).

Figure 9:
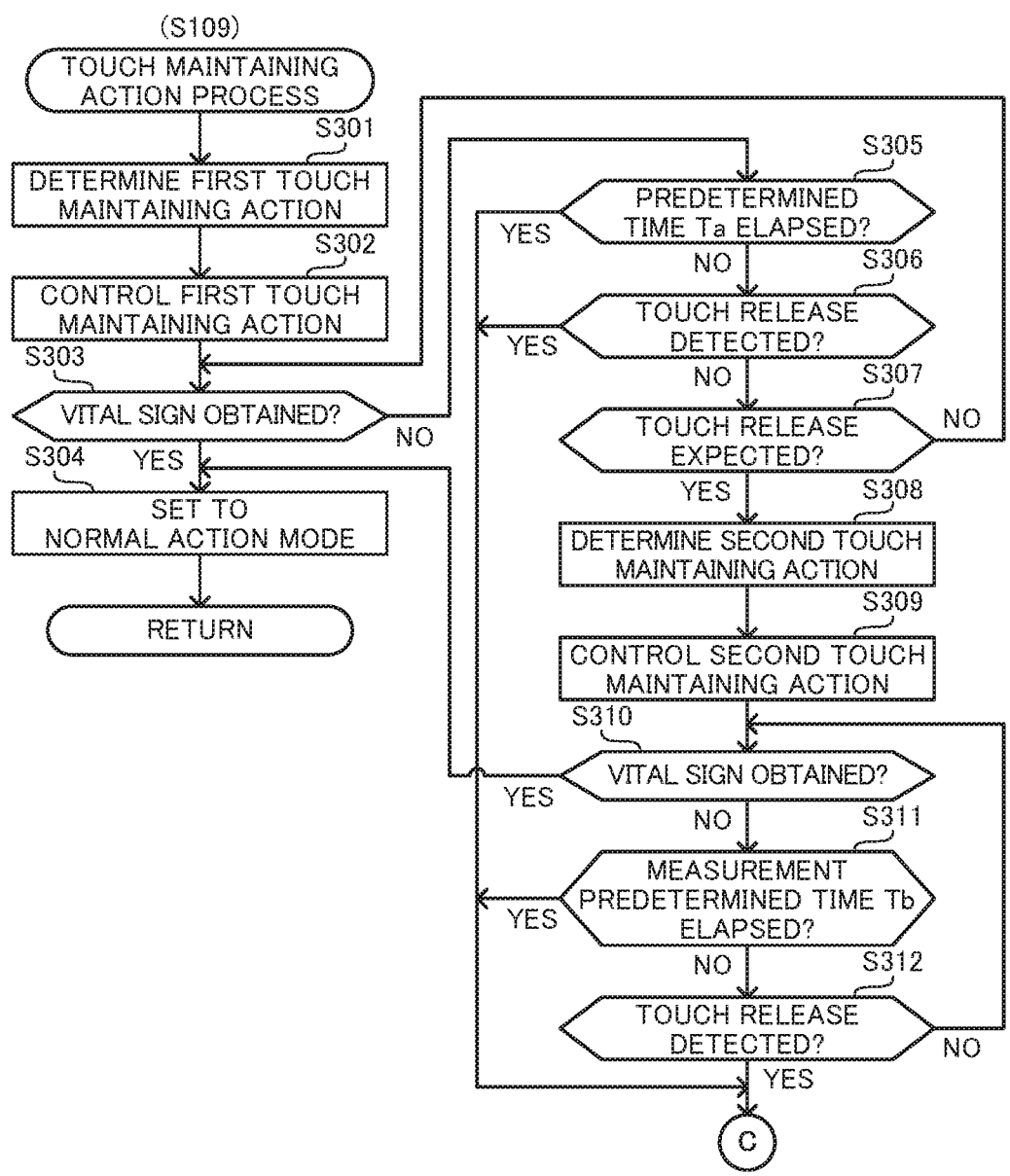
FIG. 9 is a flowchart illustrating a flow of a touch maintaining action process.

When determining that the action mode is not the normal action mode (step S108: NO), the controller 111 executes the touch maintaining action process (step S109). In this case, with reference to a flowchart that is FIG. 9, the touch maintaining action process will be described. The touch maintaining action process is a process to perform actions for maintaining the touch by the predetermined object.

The controller 111 determines the first touch maintaining action when starting the touch maintaining action process (step S301). The controller 111 refers to the touch maintaining action determining table illustrated in FIG. 6, and selects one of the multiple first touch maintaining actions set in the touch maintaining action determining table, thereby determining the first touch maintaining action.

Next, the controller 111 transmits the control signal based on the determined first touch maintaining action to the movement mechanism 115 and to the movable mechanism 116 to control those blocks to perform the first touch maintaining action (step S302). Hence, the robot 100 executes the first touch maintaining action as an action to maintain the predetermined object of the touch.

The controller 111 determines whether or not the measured value of the vital signs is obtained (step S303). When determining that the measured value of the vital signs is obtained (step S303: YES), the controller 111 sets and changes the action mode to the normal mode (step S304). Next, the controller 111 ends the touch maintaining action process, and progresses the process to step S115.

Conversely, when determining that the measured value of the vital sign is not obtained (step S303: NO), the controller 111 determines, after detecting the touch by the predetermined object, whether or not a predetermined time Ta has elapsed (step S305). The controller 111 determines whether or not the predetermined time Ta has elapsed by referring to the count value by the timer that has started the counting at the step S106. The predetermined time Ta corresponds to the time necessary for measuring the vital sign, and a proper time in consideration of the variability of time necessary for measurement relating to each item of the vital sign and the variability depending on the physical condition is set as appropriate.

When determining that the predetermined time Ta has not elapsed yet (step S305: NO), the controller 111 determines whether or not the touch by the predetermined object is released, that is, whether or not a release of a body part of the predetermined object (a hand, a finger, or the like) from the robot 100 is detected (step S306). The controller 111 detects the release of the touch by the predetermined object in accordance with, for example, a change in the measured value by the vital sensor in the sensor set 113.

When determining that the release of the touch by the predetermined object is not detected (step S306; NO), the controller 111 determines whether the touch release is expected (step S307). For example, the controller 111 detects a change in motion of the robot 100 and in direction thereof based on the measured data by the acceleration sensor and the angular velocity sensor in the sensor set 113, and expects that the touch by the predetermined object is likely to be released. When not expecting the touch release (step S307: NO), the controller 111 returns the process to the step S303.

Conversely, when the touch release is expected (step S307: YES), the controller 111 determines the second touch maintaining action (step S308). The controller 111 refers to the touch maintaining action determining table illustrated in FIG. 6, and selects any of the multiple second touch maintaining actions that is set in the touch maintaining action determining table, thereby determining the second touch maintaining action.

Next, the controller 111 transmits the control signal based on the determined second touch maintaining action to the movement mechanism 115 and to the movable mechanism 116 to control those to perform the second touch maintaining action (step S309). Hence, the robot 100 further executes, as the action for maintaining the touch by the predetermined object, the different second touch maintaining action from the first touch maintaining action.

After executing the second touch maintaining action in the step S309, the controller 111 determines whether or not the measured value of the vital sign is obtained (step S310). When determining that the measured value of the vital sign is obtained (step S310: YES), the controller 111 progresses the process to the step S304.

Conversely, when determining that the measured value of the vital sign is not obtained (step S310: NO), the controller 111 determines whether or not a measurement predetermined time Tb has elapsed (step S311). When determining that the measurement predetermined time Tb has not elapsed yet (Step S311: NO), the controller 111 determines whether or not the touch release is detected (step S312). When determining that the touch release is not detected (step S312: NO), the controller 111 returns the process to the step S310, and stands by for the obtainment of the measured value of the vital sign until the predetermined time Tb elapses.

When determining that the touch release is detected (step S312: YES), or when determining as YES in any of the steps S305, S306, and S311, the controller 111 terminates the touch maintaining action process as the measured value of the vital sign not being obtained, and progresses the process to the step S103 in the touch corresponding action process.

Returning to the flowchart for the touch corresponding action process illustrated in FIG. 7, when determining that the action mode is the normal action mode in the step S108 (step S108: YES), the controller 111 determines whether or not the measured value of the vital sign is obtained (step S110). The controller 111 determines that the measured value of the vital sign is obtained when at least one of the body temperature, the pulse rate, and the blood pressure is obtained.

When determining that the measured value of the vital sign is not obtained (step S110: NO), the controller 111 determines, after detecting the touch by the predetermined object, whether or not the predetermined time Ta has elapsed (step S111). The controller 111 determines whether or not the predetermined time Ta has elapsed by referring to the count value by the timer that has started the counting in the step S106. When determining that the predetermined time Ta has elapsed (step S111: YES), the controller 111 progresses the process to the step S114 as the measured value of the vital sign not being obtained within the predetermined time Ta.

When determining that the predetermined time Ta has not elapsed yet (step S111: NO), the controller 111 determines whether or not the touch release by the predetermined object is detected (step S112). When determining that the touch release by the predetermined object is not detected (step S112: NO), the controller 111 returns the process to the step S110.

Conversely, when determining that the touch release by the predetermined object is detected (step S112: YES), the controller 111 sets and changes the action mode to the touch maintaining action mode since the measured value of the vital sign was not obtainable due to the insufficient touch time by the predetermined object (step S113). Next, the controller 111 resets the timer (step S114), and returns the process to the step S103.

When determining that the vital sign is obtained in the step S110 (step S110: YES), the controller 111 determines the measured value of the vital sign obtained at the present time (step S115). The controller 111 refers to the determining criterion table illustrated in FIG. 3 and stored in the memory 114, and determines in which classification the measured value of the vital sign obtained at the present time falls "within normal range", "exceeding upper limit threshold", or "exceeding lower limit threshold".

Next, the controller 111 determines the corresponding action of the robot 100 based on the determination result in the step S115 (step S116). The controller 111 refers to the corresponding action determining table illustrated in FIG. 4, and determines the corresponding actions by the robot 100. The controller 111 may select the corresponding action to any item when all determination results for the items of the vital signs (the body temperature, the pulse, and the blood pressure) fall in "within normal range". In addition, the controller 111 may select the multiple corresponding actions, and executes those actions in sequence or in parallel. Conversely, when there is a determination result for each item of the vital signs that falls in "exceeding upper limit threshold" or "exceeding lower limit threshold", the corresponding action to such an item may be selected with a priority.

Subsequently, the controller 111 transmits the control signal based on the determined corresponding action to the movement mechanism 115 and to the movable mechanism 116, to control those to perform the corresponding action (step S117).

After executing the process in the step S117, the controller 111 adds the measured value of the vital sign obtained at the present time, the determined result thereof, various actions executed at the present time, and the like, to the record table, and updates the table (step S118). Next, the controller 111 resets the timer (step S119), and returns the process to the step S103.

As described above, according to this embodiment, the robot 100 obtains, in response to the touch by predetermined object, biometric information of the predetermined object, and executes the health support based on the determination result on the measured value. More specifically, the robot 100 obtains, in response to the touch by the predetermined object, the measured value of the vital sign as the biometric information, and based on the compared result between the measured value and the present determining criterion, executes various actions as natural behaviors relative to the action by the predetermined object, thereby supporting the predetermined object so as to maintain or improve the health condition to the normal condition. Therefore, according to the robot 100, the predetermined object can continuously have the health support without having a consciousness of a diagnosis.

In addition, the robot 100 executes the touch maintaining action as the action for maintaining as long as possible the touch by the predetermined object. This enables the robot 100 to stably obtain the measured values of the vital signs from the predetermined object, and to execute the continuous health support.

The present disclosure is not limited to the above embodiment, and various changes and modifications can be made thereto. The above embodiment may be modified as follows.

For example, the robot 100 may have a function of recognizing the multiple predetermined objects, and perform different actions for respective predetermined objects. For example, the robot 100 may be provided with a face recognizer that recognizes the face of the predetermined object, and may habitually execute an action unique to each predetermined object. In addition, in view of, for example, a master-servant relationship between the multiple predetermined objects and a dependent reltionship, the robot 100 may determine an action to be executed relative to each predetermined object. Still further, in view of, for example, weather, temperature, humidity, and the like, the robot 100 may determine an action to be executed relative to the predetermined object.

For example, in the above embodiment, in order to simplify the description, the description has been given of an example case in which when the controller 111 can obtain at least any of the body temperature, the pulse, and the blood pressure via the vital sensor in the sensor set 113, the controller 111 determines that the measured value of the vial sign is obtained. When, however, regardless of, for example, the insufficient touch time by the predetermined object, at least one of the body temperature, the pulse, and the blood pressure among the measured values of the vital sign obtained via the vital sensor in the sensor set 113 is not obtainable, the controller 111 may set the action mode to the touch maintaining action mode so as to determine and execute the touch maintaining action enabling an obtainment of at least the measured value for the item not obtained last time. In this case, for example, in the touch maintaining action determining table illustrated in FIG. 6, the touch maintaining action (the first touch maintaining action and the second touch maintaining action) to obtain such a measured value for each item of the vital sign may be set as appropriate, and the controller 111 may select the touch maintaining action corresponding to the not-obtained item of the vital sign with priority.

In addition, for example, in the step S111 in the flowchart for the touch corresponding action process illustrated in FIG. 7, when the predetermined time Ta has elapsed (step S111: YES), the process is simply progressed to the step S114 as the measured value of the vital sign not being obtained within the predetermined time although the touch by the predetermined object is maintained, but an action to obtain at least one of the body temperature, the pulse, and the blood pressure may be additionally performed. In this case, for example, the above scheme of executing the touch maintaining action may be employed.

For example, in the above embodiment, a determination on in which classification the measured value of the vital sign obtained at the present time falls "within normal range", "exceeding upper limit threshold", and "exceeding lower limit threshold" is made, and the action corresponding to this determination result is executed. However, the physical condition and the psychological condition may be classified into multiple conditions in in accordance with the numerical value of the vital sign (for example, the physical condition may be classified into "good", "normal", "disorder", and the psychological condition may be classified into "excited", "normal", "calm", and the like), and the action corresponding to each condition may be executed in accordance with into which classification the measured value of the vital sign obtained from the predetermined object falls.

Still further, an activity condition of the predetermined object may be determined in accordance with a change in the measured value of the vital sign, and an action corresponding to the determined condition may be executed. For example, the activity condition of the predetermined object may be classified into a awaking condition (awake condition) in which the predetermined object is awake and active, a sleeping condition (sleep condition), and a sleeping onset condition in which the predetermined object is attempt to sleep (sleep onset condition), and when the pulse having the tempo gradually slowed is detected, as the predetermined object being in the sleep onset condition, music with a slower tempo than that of the pulse may be transmitted by vibration. Next, after a predetermined time has elapsed, when the pulse having the stable tempo is detected, as the predetermined object being in the sleep condition, the vibration may be terminated.

For example, in the above embodiment, the determining criteria for the measured value of the vital sign is set to be a value obtained by multiplying the average value by the upper limit thresholds and lower limit thresholds at the predetermined rate. However, the determining criteria may be set by other schemes. As for the upper limit thresholds and lower limit thresholds, for example, the center of an average value of the measured values of the vital signs may be taken, and the upper limit value and the lower limit value within the range obtained by adding or subtracting a standard deviation value relative to the average value may be set.

In addition, as the determining criteria for the measured value of the vital signs, a reference value other than the upper limit thresholds and lower limit thresholds may be set, and a different action may be executed based on a compared result between the reference value and the measured value of the vital sign obtained at the present time. For example, a first predetermined value and a second predetermined value (a value smaller than the first predetermined value) within the range between the upper limit thresholds and the lower limit thresholds may be set, when the measured value of the pulse is equal to or greater than the first predetermined value (active condition), the hand 107 and the legs 108 are changed so as to have a greater motion, and when the measured value of the pulse is less than the first predetermined value (calm condition), the hand 107 and the legs 108 are changed so as to have a smaller motion. Thus, by tuning the action by the robot 100 with the condition of the predetermined object (paging), a formation of familiarity and credibility to the robot 100 from the predetermined object is expected.

For example, in the above-described embodiment, in the steps S110 to S113 in the touch corresponding action process illustrated in the flowchart that is FIG. 7, after the touch by the predetermined object is detected, when the measured value of the vital sign is not obtained until the predetermined time Ta has elapsed, the action mode is changed from the normal mode to the touch maintaining action mode. However, under a condition in which a phenomenon continuously or intermittently occurs such that vital signs cannot be obtained due to the insufficient touch time by the predetermined object, the action mode may be changed from the normal action mode to the touch maintaining action mode. In addition, in the touch maintaining action mode, when the vital sign is continuously or intermittently obtained, the action mode may be changed from the touch maintaining action mode to the normal action mode.

For example, in the above embodiment, the memory 114 of the robot 100 stores various tables necessary to determine the execution action. However, these pieces of data may be stored in an external memory device. The robot 100 may obtain, as appropriate, necessary data from the external memory device communicable via a communication network. In addition, in the above embodiment, the controller 111 of the robot 100 controls the action of each component. However, the robot 100 may obtain an instruction command from an external device, and execute an action in accordance with the obtained instruction command.

For example, the robot 100 may obtain detection data, and the like, from various sensors disposed at an external side in addition to the sensor built in the robot 100.

In the above embodiment, the action program to be executed by the CPU of the controller 111 is stored in the ROM, or the like, beforehand. However, the present disclosure is not limited to this case, and the action program for executing the above various processes may be implemented in a conventional general-purpose computer, framework, workstation, or the like so as to function as the robot according to the above-described embodiment.

How to provide such a program is optional, and for example, may be distributed in a manner stored in a non-transitory computer-readable recording medium (flexible disk, compact disc (CD)-ROM, digital versatile disc (DVD)-ROM, or the like), or the program may be stored in a storage over a network like the Internet, and downloaded.

Still further, when the above processes are executed in a manner shared by an operating system (OS) and an application program, or, executed in a cooperative manner by the OS and the application program, only the application program may be stored in the non-transitory recording medium or storage. Yet still further, the program may be superimposed on carrier waves, and distributed via the network. For example, the above program may be posted on a bulletin board system (BBS) over the network, and distributed via the network. Next, by launching the program and executing under the control of the OS like the other application programs, the above processes may be executed.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

What is claimed is:

1. A robot comprising a processor and body parts:
   wherein the processor is configured to:
      obtain biometric information of an object from a touch part of the body parts of the robot touched by the object without requesting the object to touch the robot, wherein the biometric information is obtained by the touch of the object;
      determine the biometric information obtained;
      control the robot based on a determined result;
      control, in a case that the biometric information is not obtained due to an insufficient touch time by the object, at least one of the body pails of the robot to perform an action to welcome the touch by the object as a first maintaining action for maintaining the object to touch in such a way that the touch time by the object becomes equal to or longer than a time period necessary to obtain the biometric information;
      determine that the touch by the object is likely to be released; and
      control, in a case that the first maintaining action has been performed and the processor determine that the touch by the object is likely to be released, the at least one of the body parts, at least another one of the body parts, or both, of the robot to perform a second maintaining action that is different from the first maintaining action and requests the object to touch the robot.

2. The robot according to claim 1, wherein the processor is further configured to set a determining criterion relating to the biometric information for each of the objects, and determines the biometric information based on a compared result between the biometric information obtained and the determining criterion.

3. The robot according to claim 2, wherein the processor sets an upper limit threshold and a lower limit threshold based on an average value of measured values indicated by the biometric information as the determining criteria, and determines whether or not the measured value indicated by the biometric information obtained falls within a range between the upper limit threshold and the lower limit threshold.

4. The robot according to claim 2, wherein the processor updates and sets the determining criterion every time the processor obtains the biometric information by a predetermined number of times.

5. The robot according to claim 3, wherein the processor updates and sets the determining criterion every time the processor obtains the biometric information by a predetermined number of times.

6. The robot according to claim 3, wherein the processor is further configured to report information based on the determined result to the object, wherein in a case that the determiner determines that the measured value indicated by the biometric information obtained by the obtainer does not fall in the range between the upper limit threshold and the lower limit threshold, the processor reports the measured value to the object.

7. The robot according to claim 6, wherein the processor determines improved behavior so as to cause the measured value indicated by the biometric information of the object to fall in the range between the upper limit threshold and the lower limit threshold, and reports the improved behavior together with the measured value to the object.

8. The robot according to claim 1, wherein the processor is further configured to change temperature of the robot, wherein the processor controls the temperature changer based on the determined result.

9. The robot according to claim 1, wherein the processor is further configured to recognize a face of the object, wherein the processor changes control of the robot in accordance with a recognized result.

10. The robot according to claim 9, wherein: the processor recognizes the faces of a plurality of the objects; and the processor determines a master-servant relationship between the plurality of objects or a dependent relationship therebetween based on the recognized result, and changes the control.

11. The robot according to claim 1, wherein the processor is further configured to acquire environmental information including weather, temperature, or humidity, and changes the control based on the environmental information.

12. The robot according to claim 1, wherein the object is a human or an animal.

13. A robot control method comprising:
obtaining biometric information of an object in accordance with a touch by the object to the robot without requesting the object to touch the robot, the biometric information being obtained by the touch of the object;
determining the obtained biometric information; and
controlling the robot based on a determined result by the determination on the biometric information;
controlling, in a case that the biometric information is not obtained due to an insufficient touch time by the object, the robot to perform an action to welcome the touch by the object as a first maintaining action for maintaining the object to touch in such a way that the touch time by the object becomes equal to or longer than a time period necessary to obtain the biometric information;
determining that the touch by the object is likely to be released; and
controlling, in a case that the first maintaining action has been performed and the processor determines that the touch by the object is likely to be released, the robot to perform a second maintaining action that is different from the first maintaining action and requests the object to touch the robot.

14. A non-transitory computer readable recording medium having stored therein a program that causes a computer to accomplish a robot control function, the program causing the computer of the robot to:
obtain biometric information of an object in accordance with a touch by the object to the robot without requesting the object to touch the robot, the biometric information being obtained by the touch of the object;
determine the obtained biometric information;
control the robot based on a determined result by the determination on the biometric information;
control, in a case that the biometric information is not obtained due to an insufficient touch time by the object, the robot to perform an action to welcome the touch by the object as a first maintaining action for maintaining the object to touch in such a way that the touch time by the object becomes equal to or longer than a time period necessary to obtain the biometric information;
determine that the touch by the object is likely to be released; and
control, in a case that the first maintaining action has been performed and the processor determines that the touch by the object is likely to be released, the robot to perform a second maintaining action that is different from the first maintaining action and requests the object to touch the robot.

* * * * *